(12) United States Patent
Meythaler

(10) Patent No.: US 6,503,931 B1
(45) Date of Patent: Jan. 7, 2003

(54) USE OF 4-AMINO PYRIDINE FOR TREATMENT OF PERIPHERAL NEUROPATHIES

(75) Inventor: Jay M. Meythaler, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/913,082

(22) PCT Filed: Feb. 9, 2000

(86) PCT No.: PCT/US00/03396
§ 371 (c)(1),
(2), (4) Date: Aug. 9, 2001

(87) PCT Pub. No.: WO00/47210
PCT Pub. Date: Aug. 17, 2000

Related U.S. Application Data

(60) Provisional application No. 60/119,273, filed on Feb. 9, 1999.

(51) Int. Cl.⁷ ................................................. A61K 31/44
(52) U.S. Cl. ........................................................ 514/352
(58) Field of Search ........................................... 514/352

(56) References Cited

U.S. PATENT DOCUMENTS 4,855,290 A * 8/1989 Fisher et al. ................. 514/278
5,668,117 A * 9/1997 Shapiro ........................ 514/55

OTHER PUBLICATIONS

Windebank et al., "Treatment of stable chronic demyelinating polyneuropathy with 3,4–diaminopyridine", Mayo Clinic Proceeding, 1995, 70 (6) 532–9.*

* cited by examiner

*Primary Examiner*—Zohreh Fay
*Assistant Examiner*—Brian-Yong S. Kwon
(74) *Attorney, Agent, or Firm*—Gifford, Krass, Groh, Sprinkle, Anderson & Citkowski, P.C.

(57) ABSTRACT

The present invention provides methods of using aminopyridine compounds to treat peripheral nervous system demyelinating diseases including Guillain-Barre Syndrome, diabetes mellitus, and hereditary sensory-motor neuropathies.

5 Claims, 3 Drawing Sheets

USE OF 4-AMINO PYRIDINE FOR TREATMENT OF PERIPHERAL NEUROPATHIES

RELATED APPLICATION

This application claims priority of U.S. Provisional Patent Application No. 60/119,273 filed Feb. 9, 1999 which is incorporated herein by reference.

FIELD OF THE INVENTION

The subject invention relates to the treatment of peripheral neuropathies and, more specifically, to the treatment of demyelinating peripheral neuropathies.

BACKGROUND OF THE INVENTION

By way of background, demyelinating neuropathies or diseases can occur in both the central nervous system and peripheral nervous system. Multiple sclerosis (MS) is a degenerative and inflammatory neurological disease which affects the central nervous system and, more specifically, the myelin sheath. MS causes demyelination of nerve fibers which results in a short-circuiting of nerve impulses and thus a slowing or blocking of transmission along the nerve fibers with associated disabling symptoms including spasticity, loss of motor strength, and painful dysaesthesias (neurogenic pain). In contrast, with peripheral demyelinating neuropathy, spasticity does not occur; however, weakness and neurogenic pain are problematic. Peripheral neuropathies are associated with a number of diseases, syndromes, or conditions including but not limited to acquired diseases or conditions including Guillain-Barre Syndrome (GBS), chronic demyelinating polyradiculoneuropathy (CIDP), diabetic mellitus (prevalence of diabetic neuropathy alone is over one million in the United States), or the hereditary sensory-motor neuropathies (Charcopt-Marie-Tooth disease, Friedrich's ataxia, porphyria, lipoprotein neuropathies, and familial amyloid neuropathies).

U.S. Pat. No. 5,540,938 to Masterson et al., issued Jul. 30, 1996, and assigned to Elan Corporation discloses a method for the treatment of neurological diseases characterized by central nervous system demyelination such as MS and Alzheimer's disease, by the administration of mono- or di-aminopyridine to a patient having the central nervous system demyelinating disease. The Masterson et al. patent only teaches the amelioration of symptoms associated with the central nervous system demyelating diseases and does not describe the use of aminopyridines for the treatment of peripheral nervous system demyelating diseases or their symptoms.

U.S. Pat. No. 5,545,648 to Hansebout et al., issued Aug. 13, 1996, and assigned to the Canadian Spinal Research Organization, discloses the use of 4-aminopyridine for the reduction of chronic pain and spasticity in spinal cord injured patients. However, the Hansebout et al. patent only discloses the use of 4-aminopyridine for the treatment of central nervous system diseases and injuries such as spinal cord injury. (See also, Segal et al. (1998) "4-Aminopyridine Alters Gait Characteristics and Enhances Locomotion in Spinal Cord Injured Humans," *The Journal of Spinal Cord Medicine*, Vol. 21, pp. 200–204.

It is interesting to note that, in general, central nervous system demyelinating diseases such as MS do not cross over to affect the peripheral nervous system as the peripheral myelin is different in both its structure and response to antibodies than is, the central nervous system myelin even though both the peripheral myelin and central myelin provide many of the same physiologic characteristics to the underlying nerve. Furthermore, peripheral nervous system demyelinating diseases usually spare the central nervous system as exemplified in GBS, diabetes mellitus, and hereditary sensory-motor neuropathies.

Accordingly, it would be advantageous and desirable to have a method for treating peripheral nervous system demyelinating diseases. The use of aminopyridines, specifically, 4-aminopyridine, shows promise in providing a drug for use in the treatment of peripheral nervous system demyelinating diseases, such as GBS, which has previously not been identified in the prior art. The use of 4-aminopyridine for treatment of peripheral nervous system demyelinating diseases fills a long-felt and previously unmet need by medical practitioners and those suffering from peripheral nervous system demyelinating diseases for a treatment modality which can alleviate symptoms of their diseases.

SUMMARY OF THE INVENTION

According to the subject invention, there is disclosed a method for treating a patient/subject having a peripheral nervous system demyelinating disease which includes the step of administering to a patient/subject having a peripheral nervous system demyelinating disease a therapeutically effective amount of an aminopyridine compound.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
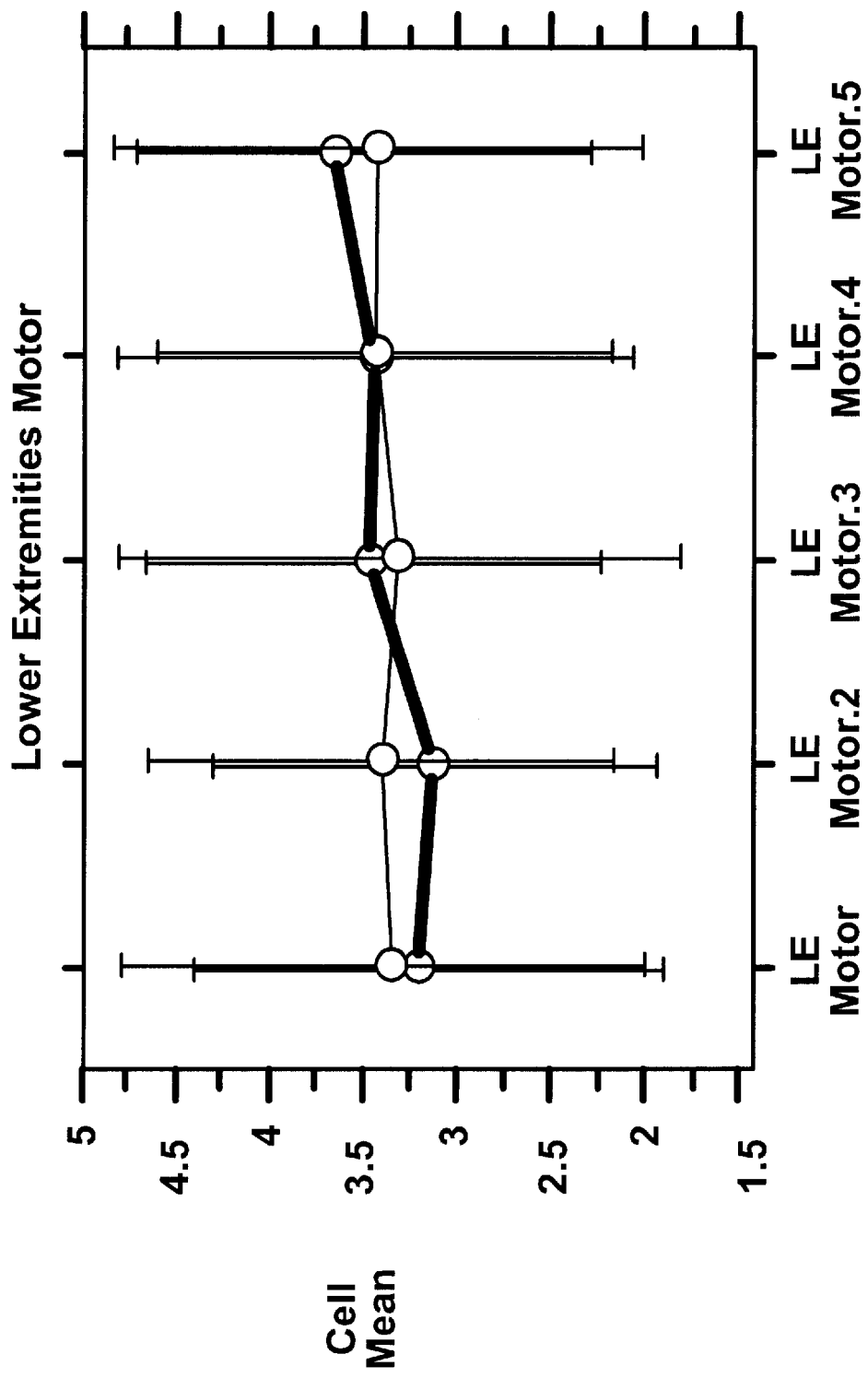
FIG. 1 is a graph illustrating lower extremity motor strength over time for both treated and untreated patients wherein the thin line represents the placebo and the thick line represents the active drug.

The present invention provides a method for treating a peripheral nervous system demyelinating disease by administering to a patient or subject having a peripheral nervous system demyelinating disease a therapeutically amount of an aminopyridine, analogs, substituted forms, derivatives of aminopyridine, or the pharmaceutically acceptable salts, esters, amides, and prodrugs thereof.

The terms "patient" and "subject" mean all animals including humans. Examples of patients or subjects include humans, cows, dogs, cats, goats, sheep, and pigs.

The term "substituted" means that the base organic radical has one or more substituents. For example, mono- or di-amino substituted pyridine such as 3,4-diaminopyridine.

Those skilled in the art are easily able to identify patients or subjects having a peripheral nervous system demyelinating disease or condition. For example, patients who are suffering from the Guillain-Barre syndrome (GBS) or diabetes mellitus.

A therapeutically effective amount is an amount of an aminopyridine compound, that when administered to a patient or subject, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intrathecally, intra-vaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solution are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Barge et al., "Pharmaceutical Salts," *J. Pharm. Sci.*, 1977, 66:1–19 which is incorporated herein by reference.).

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compounds of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

Experimental Data

Study Design

This was a Phase I double-blind, placebo controlled, crossover, dose escalating study in subjects with GBS similar to those proposed for MS and SCI. An initial trial of ten patients will be randomized to none of the two treatment sequences (A or B) as shown below.

Population

The study population consists of subjects with GBS injury whose neurological status has been stable for at least eighteen months. Ten subjects will be enrolled.

Inclusion Criteria

Male or female, 18 to 75 years of age, irrespective of race.

The subject is able to and has voluntarily given informed consent prior to the performance of any study specific procedures.

The subject has neurological impairment secondary to GBS which has been stable for at least eighteen months.

The subject is unable to ambulate more than 200 feet without assistive devices.

The subject is able and willing to comply with the protocol.

The subject has profound pain.

The subject has abnormal motor or sensory nerve conduction velocities in at least two tested nerves.

Exclusion Criteria

The subject is a pregnant female (as determined by a urine pregnancy test), a lactating female, or a female of childbearing potential not using one of the following methods of birth control (oral contraceptive, implantable conception device or injectable contraceptive agent, barrier method of contraception) or not surgically sterilized.

The subject has a history of seizures.

The subject has a known allergy to pyridine-containing substances.

The subject has evidence of upper motor neuron involvement.

The subject has any medical condition, including psychiatric disease, which would interfere with the interpretation of the study monitor.

The subject has been on concomitant medications at a stable dose/regimen for less than three weeks, and/or the stable dose/regimen of concomitant medications is expected to be changed during the course of the study.

The subject has a history of drug or alcohol abuse within the past year.

The subject has received an investigational drug within thirty days prior to the screening visit.

The subject has taken 4-aminopyridine in the past, whether through participation in a previous study or self-medication.

Objective Neurological Functional Assessment

Variables to be Collected: The measures of neurological status reported for this study are:

Motor strength was rated on the traditional 0–5 ordinal scale:

0—absent motor strength

1—trace motor strength

2—can move the specified joint but only with gravity eliminated

3—can move the joint against gravity but not against any opposing force

4—can move the joint against opposing force but the strength is not normal for the person or symmetrical 5—normal motor strength This scale was employed to measure the following motor strength for each of these joint motions on both the right and the left sides: hip flexion, hip adduction, hip abduction, knee flexion, knee extension, ankle dorsi-flexion, ankle plantar flexion, shoulder abduction, elbow extension, elbow flexion, wrist flexion, and wrist extension.

In addition, the following criteria were also rated:

Hand grip strength was measured on a hand dynamometer that had been calibrated. Each patient was given three trials separated by thirty second rest periods and the strongest of the three measurements was recorded for each hand.

In addition, serum laboratories were drawn at the beginning of the study and every week of the study. The serum laboratories included glucose, blood urea nitrogen, creatinine, uric acid, calcium, total protein, albumin, phosphate, total bilirubin, cholesterol, LDH, SGOT/AST, alkaline phosphatase, hematocrit, hemoglobin, red blood cell count, platelet count, and white blood cell count with differential.

Treatment variables to be collected include method of bladder management as well as usage of a ventilator, plasmapheresis, steroids, and intravenous immunoglobulin (IVIg) as these variables are related to the severity of disease (Zelig G, Ohry A, Shemsesh Y, Bar-On Z, Blumen M, Brooks M E. The rehabilitation of patients with severe Guillain-Barre syndrome. *Paraplegia* 1988; 26; 250–254; Meythaler J M, DeVivo M J, Braswell W C. Rehabilitation outcomes of patients who have developed Guillain-Barre Syndrome. *Am J Phys Med Rehabil* 1997; 76:411–419). Information will also be collected on GBS subtype, GBS etiology, general patient demographic characteristics, relevant medical history, length of stay during acute care and rehabilitation, charges for acute care and rehabilitation, sponsors of care, and rehospitalizations (Meythaler J M. Rehabilitation of Guillain-Barre Syndrome. *Arch Phys Med Rehabil* 1997; 78:872–9; Meythaler J M, DeVivo M J, Braswel W C. Rehabilitation outcomes of patients who have developed Guillain-Barre syndrome. *Am J Phys Med and Rehabil* 1997; 76:411–9.). This data is part of the currently funded NIDRR study on GBS outcomes funded here at UAB.

Data Analysis/Database Development

The collectibility and ultimate quality of information contained in each variable is assessed both subjectively and objectively.

The entire project team reviews the reported frequency distributions, means, cross-tabulations, etc. of each variable for reasonableness. For example, if a high or low incidence of a particular complication is reported that seems inconsistent with the clinical experience of the investigators, then the definition of this variable will be reconsidered and either left unchanged, clarified or deleted as appropriate. Complications that do not occur in any cases will also be candidates for deletion, while unanticipated occurrences may be candidates for addition to the database. This procedure has been used successfully by the Model Spinal Cord Injury Systems for many years.

EMG NCS

All patients will have two upper and lower extremity motor and sensory nerve conditions (total four motor four sensory) performed at the enrollment period and at the maximal point of drug delivery in both the A and B phases. This assesses for objective improvement in nerve conduction velocity with the use of 4-AP. Nerve conduction velocities and amplitudes are performed for median and peroneal nerves.

Dosing Sequence 4-aminopyridine can be compounded. The drug was compounded locally by a pharmaceutical compounding company (Scott Wepfer Rph, The Compounding Shoppe). This compound should be stable for a few weeks.

| Sequence | week 1 | week 2 | week 3 | week 4 | week 5 | week 6 | week 7 |
|---|---|---|---|---|---|---|---|
| A | 10 mg bid | 15 mg bid | 20 mg bid | washout | placebo | placebo | placebo |
| B | placebo | placebo | placebo | washout | 10 mg bid | 15 mg bid | 20 mg bid |

The dose escalation only applies when the subject does not have dose-limiting toxicity.

Results

Eight patients were recruited for the double blind trial. There were three males and five females. One female patient fell out of the study due to the development of chronic demyelinating polyradiculoneuropathy (CIDP). This may have been partially masked by the 4-AP. The remaining seven patients, average age 57 (range 27–73), completed the double blind randomized protocol.

Motor Strength

Lower extremity strength for hip abduction, hip adduction, hip flexion, knee flexion, ankle dorsiflexion and plantar flexion increased from an average motor score of 3.2 to 3.7 (p<0.0001, Friedeman's) on the active medication as shown in FIG. 1.

Figure 2:
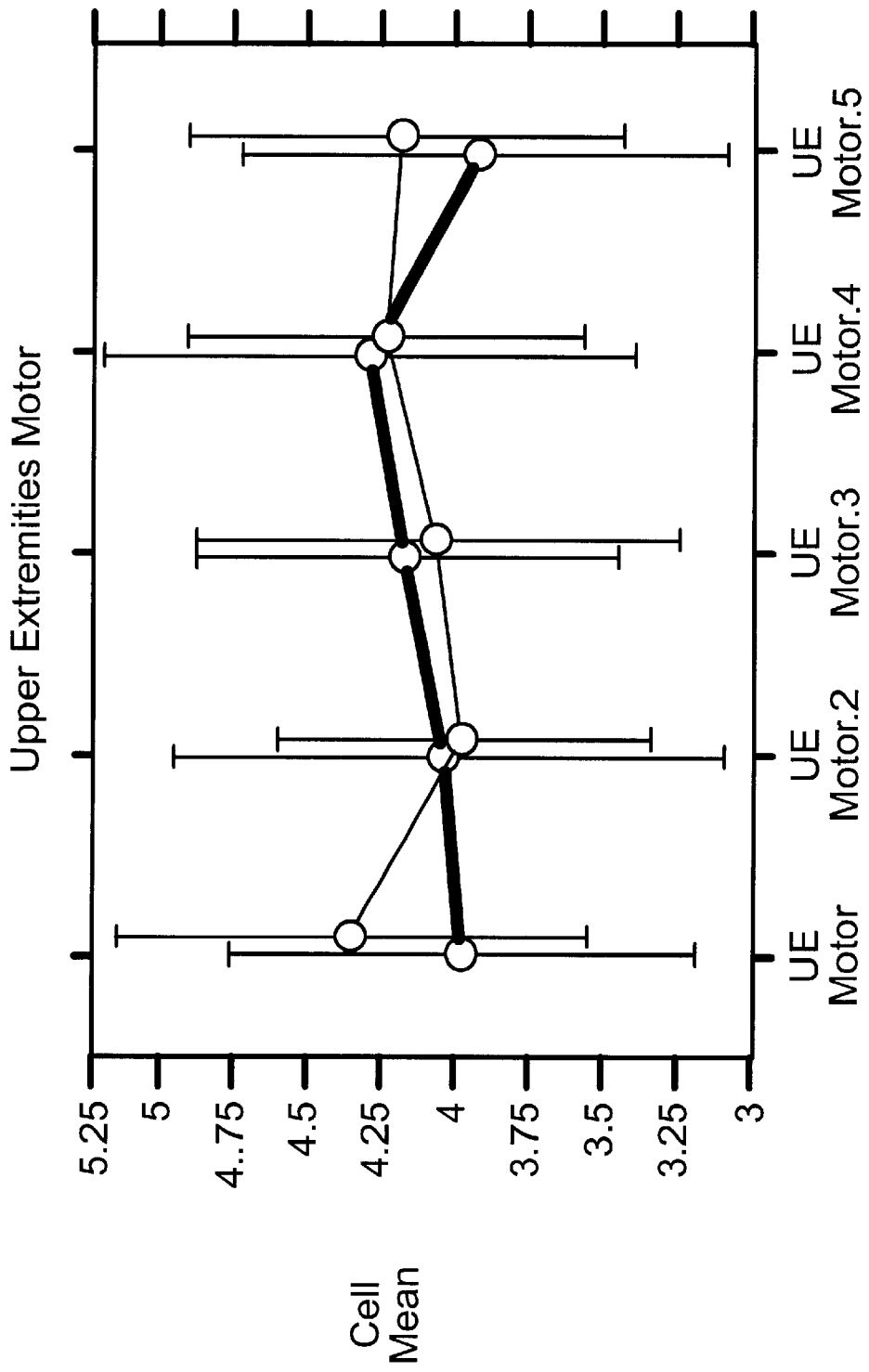
FIG. 2 is a graph illustrating upper extremity motor strength over time for untreated and treated patients wherein the thin line represents the placebo and the thick line represents the active drug.

Upper extremity strength for hip abduction, hip adduction, hip flexion, knee flexion, ankle dorsiflexion and plantar flexion increased from an average motor score of 3.2 to 3.7 (p=0.0065, Friedeman's) as shown in FIG. 2.

Figure 3:
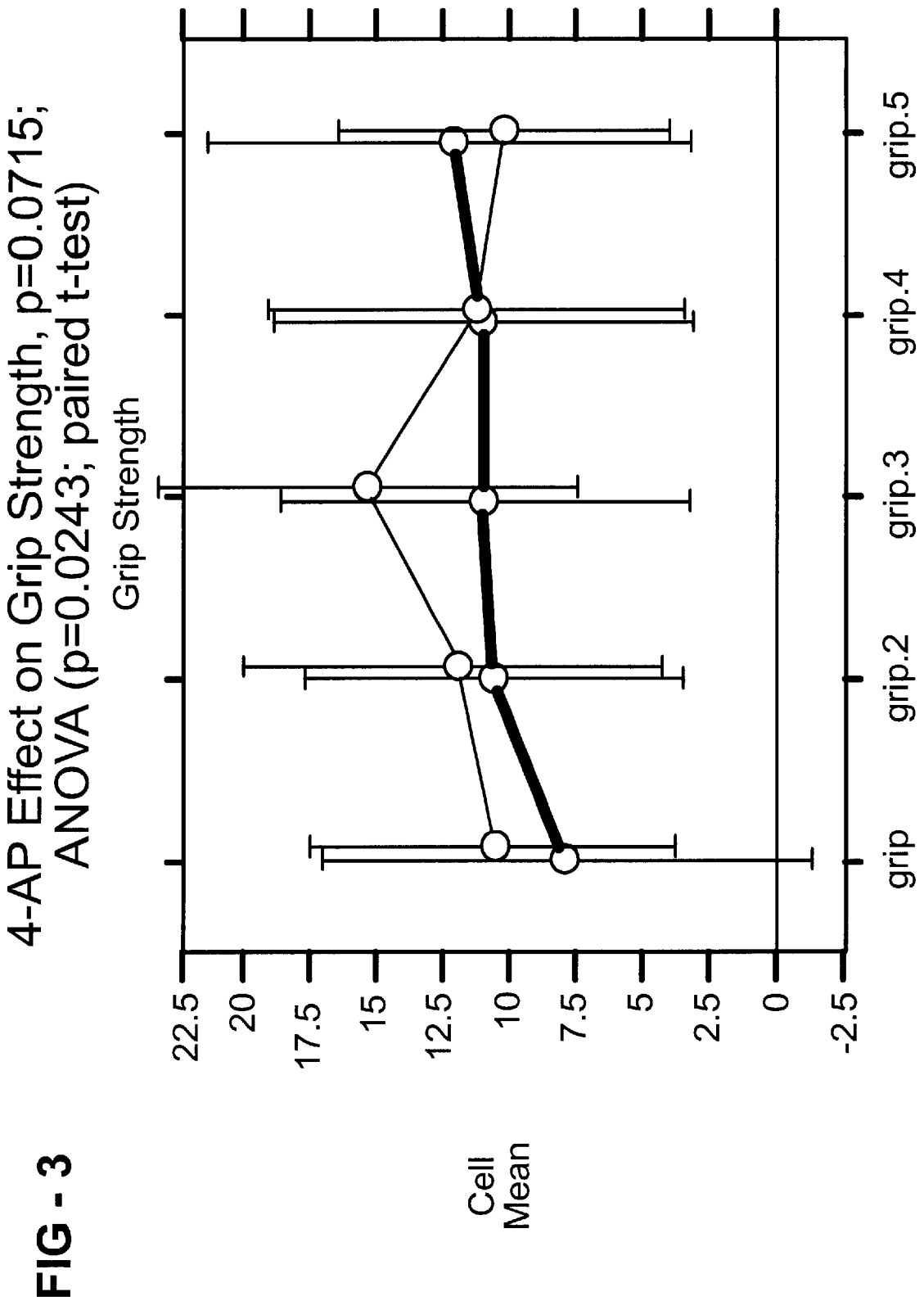
FIG. 3 is a graph illustrating grip strength over time for untreated and treated patients wherein the thin line represents the placebo and the thick line represents the active drug.

Grip strength also improved on the hand-held dynamometer. Grip strength had increased significantly from the start of the study as compared to after four weeks of treatment (p=0.0243, paired Student's t-test). Over the four week course the repeated measures ANOVA approached statistical significance (p=0.0715, ANOVA) as shown in FIG. 3.

Labs

Only three laboratories had a statistically significant change. The uric acid changed from 6.4 to 6.5, the SGOT went up from 25.1 to 27.9, and the hematocrit dropped from 42.7 to 41.6. None of these changes are clinically significant and may reflect statistical chance since so many laboratories were tested. All other laboratories had no significant change while on the active agent.

Placebo

There were no statistically significant finding while on the placebo agent. However, for those patients on the active agent first, the motor strength and grip strength continued to drop for up to two additional weeks after the one week washout period. This indicates the neural biological effects can last for more than two weeks.

In view of the teaching presented herein, other modifications and variations of the present inventions will be readily apparent to those of skill in the art. The discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed:

1. A method of treating a peripheral nervous system demyelinating disease, the method comprising administering to a patient having Guillain-Barre Syndrome a composition consisting essentially of a therapeutically effective amount of a mono-aminopyridine compound, or the pharmaceutically acceptable salts, esters, amides and prodrugs thereof.

2. A method according to claim 1, wherein the mono-aminopyridine compound is 4-aminopyridine.

3. A method according to claim 1, wherein the peripheral demyelinating disease is Guillain-Barre Syndrome.

4. A method of treating peripheral neuropathy, the method comprising administering to a patient having Guillain-Barre Syndrome a therapeutically effective amount of a mono-aminopyridine compound, or the pharmaceutically acceptable salts, esters, amides and prodrugs thereof.

5. A method according to claim 4, wherein the mono-aminopyridine compound is 4-aminopyridine.

* * * * *